United States Patent [19]

Toyoshima et al.

[11] Patent Number: 4,560,679

[45] Date of Patent: Dec. 24, 1985

[54] ORGANOSILICON COMPOUNDS AND ANTITUMOR AGENTS CONTAINING THE COMPOUND AS EFFECTIVE COMPONENT

[75] Inventors: Shigeshi Toyoshima, Tokyo; Masayasu Kurono; Ryoichi Unno, both of Nagoya; Koichi Ito, Higashi-kurume, all of Japan

[73] Assignees: Sanwa Kagaku Kenkyusho Co. Ltd., Aichi; Shin-Etsu Chemical Co. Ltd., Tokyo, both of Japan

[21] Appl. No.: 542,439

[22] Filed: Oct. 17, 1983

[30] Foreign Application Priority Data

Oct. 16, 1982 [JP] Japan ................. 57-181782

[51] Int. Cl.$^4$ .................. A61K 31/695; C07F 7/10
[52] U.S. Cl. .................. 514/63; 546/14; 549/4; 549/214; 556/410; 556/419; 556/427
[58] Field of Search .............. 546/14; 549/4, 214; 556/410, 419, 427; 424/184

[56] References Cited

U.S. PATENT DOCUMENTS 3,505,376  4/1970  Frankel et al. ............... 424/184
4,360,686  11/1977  Wang et al. ................. 556/419
4,434,161  2/1984  Barcza ...................... 424/184

FOREIGN PATENT DOCUMENTS 196841  5/1967  U.S.S.R. .................... 556/427

OTHER PUBLICATIONS

Translation of Zhurnan Obschei Khimii, (vol. 39) (No. 8) pp. 1782–1783, Aug. (1969).

Primary Examiner—Robert T. Bond
Attorney, Agent, or Firm—Bierman, Peroff & Muserlian

[57] ABSTRACT

A novel organosilicon compound represented by a formula

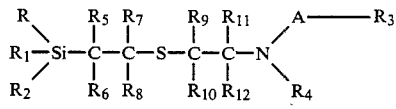

wherein A is methylene, carbonyl or sulfonyl group; R, $R_1$ and $R_2$ are alkyl group, respectively; $R_3$ is alkyl, substituted alkyl, alkenyl, phenyl, substituted phenyl, naphthyl, substituted naphthyl, pyridyl, substituted pyridyl, furyl, substituted furyl, thienyl, substituted thienyl group or cycloalkyl group together with the substituent A; $R_4$ is hydrogen, alkyl or alkenyl group; and $R_5$, $R_6$, $R_7$, $R_8$, $R_9$, $R_{10}$, $R_{11}$ and $R_{12}$ are hydrogen, alkyl or substituted alkyl, respectively, a non-toxic salt thereof, a process for the preparation of said compound or salt, as well as an antitumor agent comprising as an effective agent at least one of said compound and salt.

22 Claims, No Drawings

ORGANOSILICON COMPOUNDS AND ANTITUMOR AGENTS CONTAINING THE COMPOUND AS EFFECTIVE COMPONENT

The present invention relates to novel organosilicon compounds and non-toxic salts thereof showing an antitumor action and useful as pharmaceutical agents, a process for the preparation thereof as well as an antitumor agent comprising as an effective component at least one of the compounds and salts.

As silicon-containing compounds having the antitumor action, silatranes have hitherto been known but have a problem in use due to a relatively high toxicity thereof. At the present, therefore, it has been desired to develop a new antitumor agent which shows a good therapeutic effect and has no or reduced toxicity.

Therefore, an object of the invention is to provide novel organosilicon compounds and non-toxic salts thereof, which show a good antitumor action and a low toxicity.

Another object of the invention is to provide a process for the preparation of such compounds and salts.

A still other object of the invention is to provide a novel antitumor agent comprising as an effective component at least one of such compounds and salts.

The compounds according to the invention is shown by a formula

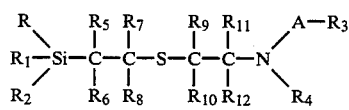
(I)

wherein A is methylene, carbonyl or sulfonyl group; R, $R_1$ and $R_2$ are alkyl group, respectively; $R_3$ is hydrogen, alkyl, substituted alkyl, alkenyl, phenyl, substituted phenyl, naphthyl, substituted naphthyl, pyridyl, substituted pyridyl, furyl, substituted furyl, thienyl, substituted thienyl group or cycloalkyl group together with the substituent A; and $R_5$, $R_6$, $R_7$, $R_8$, $R_9$, $R_{10}$, $R_{11}$ and $R_{12}$ are hydrogen, alkyl or substituted alkyl, respectively.

The alkyl group may include linear alkyl radicals having 1 to 7 carbon atoms, such as methyl, ethyl, n-propyl, n-butyl, n-pentyl, n-hexyl and n-heptyl radicals as well as branched alkyl radicals such as isopropyl, isobutyl, sec-butyl, tert-butyl, isopentyl and the like radicals. The substituted alkyl group may include halogen substituted alkyl radicals such as trifluoromethyl and the like radicals. The alkenyl group may include vinyl, allyl, isopropenyl and the like radicals. As substituents for the substituted phenyl, o-chloro, p-chloro, p-bromo, p-methyl, p-methoxy and the like radicals may be listed. The naphthyl and substituted naphthyl groups may include 1-naphthyl, 2-naphthyl, 2-hydroxy-1-naphthyl, 2-methoxy-1-naphthyl and the like radicals. The pyridyl and substituted pyridyl may include 2-pyridyl, 3-pyridyl, 4-pyridyl, 5-methyl-2-pyridyl and the like radicals. The furyl and substituted furyl may include 2-furyl, 3-furyl, 5-methyl-2-furyl and the like radicals. The thienyl and substituted thienyl may include 2-thienyl, 3-thienyl, 5-methyl-2-thienyl and the like radicals. The cycloalkyl group has 3 or more carbon atoms and may include cyclopropyl, cyclobutyl, cyclopentyl, cyclohexyl, cycloheptyl and the like radicals.

The compounds as shown by formula (I) can be prepared with use of the following compound (II), as the starting material.

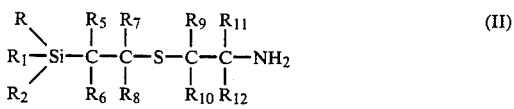
(II)

(wherein R, $R_1$, $R_2$, $R_5$, $R_6$, $R_7$, $R_8$, $R_9$, $R_{10}$, $R_{11}$ and $R_{12}$ have the meaning as referred to).

This starting material can easily be synthesized by subjecting a compound represented by a formula

(III)

wherein R, $R_1$, $R_2$, $R_5$ and $R_7$ have the meaning as referred to, to a reaction with a compound represented by a formula

(IV)

wherein $R_9$, $R_{10}$, $R_{11}$ and $R_{12}$ have the meaning as referred to, in a polar organic solvent under a ultraviolet irradiation and in the presence of a photochemical sensitizer.

(1) The compounds as shown by formula (I), wherein A is carbonyl group, can be prepared by subjecting the compound as shown by formula (II) to a reaction with an acid halide represented by a formula

$R_3$—COX    (V)

or with an acid anhydride represented by a formula

(VI)

wherein $R_3$ has the meaning as referred to and X is halogen, in same molar amount. It is, in general, preferable to carry out the reaction in a solvent, in the presence of a base and under a temperature ranging from 0° C. to a boiling point of the used solvent. As the solvent, methylene chloride, chloroform, carbon tetrachloride or the like halogenohydrocarbon; ethyl ether, tetrahydrofuran, 1,4-dioxane or the like ether; or benzene, toluene or the like aromatic hydrocarbon may be used. As the base, triethylamine, pyridine, sodium bicarbonate, potassium carbonate or the like may be used.

(2) The compounds as shown by formula (I), wherein A is methylene group, can be prepared by reducing the following compound (VII) which is prepared according to the preceding process of Item (1).

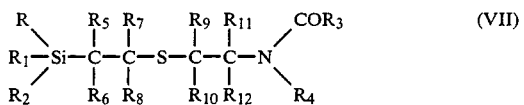

wherein R, $R_1$, $R_2$, $R_3$, $R_4$, $R_5$, $R_6$, $R_7$, $R_8$, $R_9$, $R_{10}$, $R_{11}$ and $R_{12}$ have the meaning as referred to.

The reduction of carbonyl group in the compound can be carried out with use of a suitable reducing agent in a solvent. As the reducing agent, lithium aluminum hydride, sodium aluminum hydride, aluminum hydride, sodium borohydride, sodium borohydride-triethyloxonium tetrafluoroborate or the like may be used. As the solvent, ethyl ether, tetrahydrofuran, dioxane or the like ether; methanol, ethanol or the like alcohol may be used. The reaction temperature ranging from 0° C. to a boiling point of the used solvent may be selected, by taking kinds of the raw material and solvent as well as other terms into consideration.

The compounds as shown by formula (VII) can be prepared by subjecting a compound represented by a formula

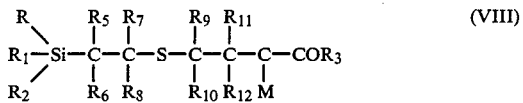

wherein R, $R_1$, $R_2$, $R_3$, $R_5$, $R_6$, $R_7$, $R_8$, $R_9$, $R_{10}$, $R_{11}$ and $R_{12}$ have the meaning as referred to and M is sodium or potassium, to a reaction with a compound represented by a formula $$X—R_4 \qquad (IX)$$

wherein $R_4$ has the meaning as referred to and X is halogen, in same molar amount.

The compounds as shown by formula (VIII) can be prepared by subjecting the compound as shown by formula (VII), wherein $R_4$ is hydrogen, to a reaction in a solvent with sodium hydride, potassium hydride or the like base. As the solvent, ethyl ether, tetrahydrofuran, dioxane or the like ether may be used. It is most preferable to carry out the reaction at a temperature of from 0° C. to the room temperature. The reaction of the compound (VIII) with the compound (IX) conveniently proceeds by using a catalytic amount of 18-crown-6 or the like crown ether and heating the reactants in the presence of a solvent. As the solvent, ethyl ether, tetrahydrofuran, dioxane or the like ether may be used. The reaction temperature may be determined by taking kinds of raw materials and solvent as well as other terms into consideration but a boiling temperature of the used solvent is usually selected therefor.

(3) N-alkyl- and N-alkenyl derivatives can be prepared by removing the acyl group in the compounds (VII) through hydrolysis thereof. The hydrolyzing reaction conveniently proceeds by using a base in the presence of a solvent. As the base, potassium hydroxide, sodium hydroxide, potassium carbonate or the like may be used. Water or an alcohol such as methanol and ethanol are most preferable as the solvent. The reaction temperature may be determined by taking kinds of the raw materials and solvent as well as other terms but a temperature of from 20° to 40° C. is usually selected therefor.

(4) N-cycloalkyl derivatives, wherein $R_3$ forms a cycloalkyl group together with the substituent A, can be prepared through a reductive amination method of the compound (II) with a cycloalkyl ketone. In general, the reaction conveniently proceeds under neutral condition, using a reducing agent and in the presence of a solvent. Sodium borohydride is most preferable as the reducing agent. As the solvent, methanol, ethanol or the like alcohol may be used. The reaction temperature may be determined by taking kinds of the raw materials and solvent as well as other terms but the temperature of from 20° to 40° C. is usually selected therefor.

(5) N-methyl derivatives can easily be prepared by converting the compound (II) into a corresponding N-formyl compound with use of formic acid and acetic anhydride, and then reducing the same with use of lithium aluminum hydride or the like reducing agent.

The N-alkyl, N-alkenyl and N-cycloalkyl derivatives to be obtained according to the methods of Items (3) and (4) are liquids having a higher boiling point but those easily form a salt with hydrochloric acid, sulfuric acid, nitric acid or the like inorganic acid as well as acetic acid, succinic acid, maleic acid, fumaric acid, tartaric acid, citric acid or the like organic acid and deposit by crystallization. Therefore, a purity thereof can be made higher through a conventional recrystallization method.

(6) The compounds as shown by formula (I), wherein A is sulfonyl group, can be prepared by subjecting the compound as shown by formula (II) to a reaction with a compound represented by a formula $$R_3—SO_2X \qquad (X)$$

wherein $R_3$ has the meaning as referred to and X is halogen, in same molar amount. This reaction can be carried out in same condition with that for the reaction of the compound (II) with the compound (V).

Each of the antitumor agents according to the invention develops its pharmaceutical action in either in oral or non-oral dosage. A tablet, capsule or granule may be selected for the oral dosage. Depending on an intended form of the pharmaceutical agent, a conventional vehicle, grossing agent, coloring agent, flavoring agent, sweetening agent and the like may be added. For preparing an injection, a pH regulator, buffering agent, stabilizer, isotonics and the like may be added to the compound according to the invention. A suppository can be prepared in a conventional manner after adding the compound according to the invention and if necessary a surfactant to a usual vehicle.

A dosing amount of the antitumor agent for a patient can be determined by taking symptoms, application form and other conditions, but in general, it is preferable to give in oral dosage 300 to 5000 mg/day for an adult. In case of injectional dosage and suppository, it is preferable to give 25 to 500 mg and 100 to 2000 mg, respectively.

The invention will now be further explained with reference to Examples and tests.

EXAMPLE 1

N-benzoyl-2-[[2-(trimethylsilyl)ethyl]thio]ethyl amine

To a solution of 4.43 g (25.0 mmol) of 2-[[2-(trimethylsilyl)ethyl]thio]ethyl amine and 2.53 g (25.0 mmol) of triethylamine in 50 ml of dichloromethane. The mixture is stirred at 25° C. for 1 hr.

The reaction mixture is washed with water and dried over sodium sulfate and evaporated to dryness.

The resulting oily residue is distilled to afford N-benzoyl-2-[[2-(trimethylsilyl)ethyl]thio]ethyl amine (6.50 g, 92.5%).

b.p.: 230° C. at 1 mm

Anal. Calcd. for: $C_{14}H_{23}NOSSi$. C 59.74; H, 8.24; N 4.98. Found: C 59.59; H 8.18; N 4.98.

IR: $\nu_{max}^{neat}$cm$^{-1}$: 3320 ($\nu_{NH}$), 2960, 2920 ($\nu_{CH}$), 1640 ($\nu_{C=O}$), 1603, 1490 ($\nu_{arom}$), 1535 ($\delta_{NH}$), 1250 ($\nu_{C-Si}$).

$^1$H-NMR (CDCl$_3$)δ: 0.01 (9H, s, —Si(CH$_3$)$_3$), 0.85 (2H, A$_2$B$_2$,

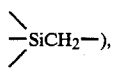

2.60 (2H, (2H, A$_2$B$_2$,

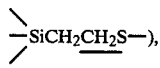

2.77 (2H, t, J=6 Hz, —SCH$_2$CH$_2$N—), 3.63 (2H, q, J=6 Hz, —CH$_2$NHCO—), 6.87 (1H, m, —NHCO—), 7.3–7.9 (5H, m, Arom.H).

mass (EI/DI) m/e: 281 (M+), 266 (—Me), 73 (base peak).

EXAMPLE 2

N-(p-chlorobenzoyl)-2-[[2-(trimethylsilyl)ethyl]thio]ethyl amine

This compound is prepared by the similar procedure as in the case of EXAMPLE 1, except for the treatment with 4.38 g (25.0 mmol) of p-chlorobenzoyl chloride instead of benzoyl chloride.

Yield: 7.40 g (94.0%).

m.p.: 42°–43° C.

Anal. Calcd. for: $C_{14}H_{22}ClNOSSi$. C 53.22; H 7.02; N 4.43. Found: C 52.94; H 7.22; N 4.42.

IR: $\nu_{max}^{KBr}$cm$^{-1}$: 3340 ($\nu_{NH}$), 2960, 2940, 2920 ($\nu_{CH}$), 1635 ($\nu_{C=O}$), 1600 ($\nu_{arom}$), 1545 ($\delta_{NH}$), 1490 ($\nu_{C=C}$), 1250 ($\nu_{C-Si}$).

$^1$H-NMR (CDCl$_3$)δ: 0.01 (9H, s, —Si(CH$_3$)$_3$) 0.85 (2H, A$_2$B$_2$,

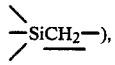

2.60 (2H, A$_2$B$_2$,

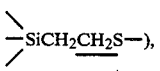

2.77 (2H, t, J=6 Hz, —SCH$_2$CH$_2$N—) 3.63 (2H, q, J=6 Hz, —CH$_2$NHCO—), 6.67 (1H, m, —NHCO—), 7.36 (2H, AA'XX', arom.H), 7.73 (2H, AA'XX', arom.H), mass (EI/DI) m/e: 315 (M+), 317 (M+2), 73 (base peak).

EXAMPLE 3

N-(1-naphthoyl)-2-[[2-(trimethylsilyl)ethyl]thio]ethyl amine

This compound is prepared by the similar procedure as in the case of EXAMPLE 1, except for the treatment with 4.76 g (25.0 mmol) of 1-naphthoyl chloride instead of benzoyl chloride.

Yield: 7.70 g (93.1%).

m.p.: 45°–46° C.

Anal. Calcd. for: $C_{18}H_{25}NOSSi$. C 65.21; H 7.60; N 4.22. Found: C 65.46; H 7.76; N 4.46.

IR: $\nu_{max}^{KBr}$cm$^{-1}$: 3340 ($\nu_{NH}$), 2960, 2920 ($\nu_{C-H}$), 1640 ($\nu_{C=O}$), 1540 ($\delta_{NH}$), 1250 ($\nu_{C-Si}$).

$^1$H-NMR (CDCl$_3$)δ: 0.01 (9H, s, —Si(CH$_3$)$_3$) 0.85 (

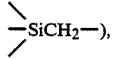

2.63

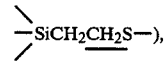

2.83 (2H, t, J=6 Hz, —SCH$_2$CH$_2$N—), 3.62 (2H, q, J=6 Hz, —CH$_2$NHCO—), 6.50 (1H, m, —NHCO—), 7.3–8.5 (7H, m, arom.H).

mass (EI/DI) m/e: 331 (M+), 73 (base peak).

EXAMPLE 4

N-nicotinoyl-2-[[2-(trimethylsilyl)ethyl]thio]ethyl amine

This compound is prepared by the similar procedure as in the case of EXAMPLE 1, except for the treatment with 4.45 g (25.0 mmol) of nicotinic acid chloride hydrochloride instead of benzoyl chloride and 5.05 g (50.0 mmol) of triethylamine.

Yield: 6.50 g (92.2%).

b.p.: 248° C. (1 mm).

Anal. Calcd. for: $C_{13}H_{22}N_2OSSi$. C 55.28; H 7.85; N 9.92. Found: C 54.81; H 8.14; N 9.79.

IR: $\nu_{max}^{neat}$cm$^{-1}$: 3320 ($\nu_{NH}$), 2960, 2920 ($\nu_{CH}$), 1655 ($\nu_{C=O}$), 1595 ($\nu_{C=C}$), 1545 ($\delta_{NH}$), 1480 ($\nu_{C=C}$), 1250 ($\nu_{C-Si}$).

$^1$H-NMR(CDCl$_3$)δ: 0.01 (9H, s, —Si(CH$_3$)$_3$), 0.85 (2H, A$_2$B$_2$,

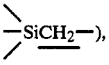

2.60 (2H, A$_2$B$_2$, 2.80 (2H, t, J=6 Hz, —SCH₂CH₂N—), 3.65 (2H, q, J=6 Hz, —CH₂NHCO—), 7.05 (1H, m, —NHCO—), 7.34 (1H, dd, J=5 Hz, 8 Hz,

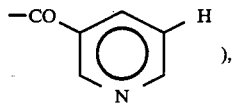
), 8.10 (1H, dt, J=2 Hz, 8 Hz,

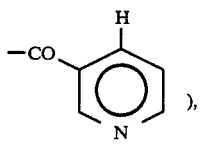
), 8.67 (1H, dd, J=2 Hz, 5 Hz,

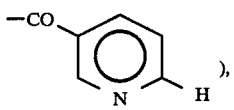
), 8.97 (1H, d, J=2 Hz,

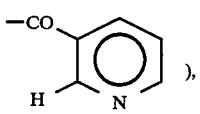
), mass (EI/DI) m/e: 282 (M+), 73 (base peak).

EXAMPLE 5

N-(2-furoyl)-2-[[2-(trimethylsilyl)ethyl]thio]ethyl amine

This compound is prepared by the similar procedure as in the case of EXAMPLE 1, except for the treatment with 3.26 g (25.0 mmol) of 2-furoyl chloride instead of benzoyl chloride.

Yield: 6.20 g (91.5%).
b.p.: 225° C. (1 mm).
Anal. Calcd. for: $C_{12}H_{21}NO_2SSi$. C 53.10; H 7.80; N 5.16. Found: C 52.55; H 8.04; N 5.13.
IR: $\nu_{max}^{neat}$ cm⁻¹: 3320 ($\nu_{NH}$), 2960, 2920 ($\nu_{CH}$), 1650 ($\nu_{C=O}$), 1595, 1575 ($\nu_{C=C}$), 1530 ($\delta_{NH}$), 1480 ($\nu_{C=C}$), 1250 ($\nu_{C-Si}$).
¹H-NMR(CDCl₃)δ: 0.01 (9H, s, —Si(CH₃)₃), 0.85 (2H, A₂B₂,

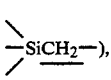
), 2.60 (2H, A₂B₂,

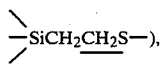
), 2.77 (2H, t, J=6 Hz, —SCH₂CH₂N—), 3.61 (2H, q, J=6 Hz, —CH₂NHCO—) 6.46 (1H, dd, J=2 Hz, 3.6 Hz,

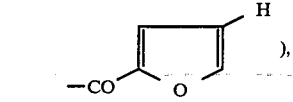
), 6.82 (1H, m, —NHCO—), 7.10 (1H, d, J=3.6 Hz,

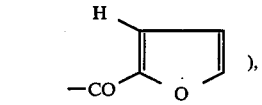
), 7.42 (1H, m,

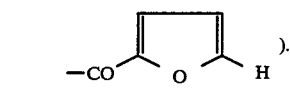
).

mass (EI/DI) m/e: 271 (M+), 73 (base peak).

EXAMPLE 6

N-thenoyl-2-[[2-(trimethylsilyl)ethyl]thio]ethyl amine

This compound is prepared by the similar procedure as in the case of EXAMPLE 1, except for the treatment with 3.67 g (25.0 mmol) of thenoyl chloride instead of benzoyl chloride.

Yield: 6.60 g (92.1%).
b.p.: 230° C. (1 mm).
Anal. Calcd. for: $C_{12}H_{21}NOS_2Si$. C 50.13; H 7.36; N 4.87. Found: C 49.35; H 7.55; N 4.81.
IR: $\nu_{max}^{neat}$ cm⁻¹: 3320 ($\nu_{NH}$), 2960, 2920 ($\nu_{CH}$), 1630 ($\nu_{C=O}$), 1550 ($\delta_{NH}$), 1515 ($\nu_{C=C}$), 1420 ($\nu_{C=C}$), 1250 ($\nu_{C-Si}$).
¹H-NMR(CDCl₃)δ: 0.01 (9H, s, —Si(CH₃)₃), 0.85 (2H, A₂B₂,

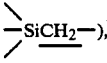
), 2.60 (2H, A₂B₂,

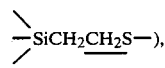
), 2.77 (2H, t, J=6 Hz, —SCH₂CH₂N—), 3.61 (2H, q, J=6 Hz, —CH₂NHCO—), 6.70 (1H, m, —NHCO—) 7.03 (1H, m, 7.44 (1H, m,

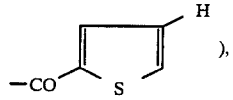), 7.50 (1H, dd, J=1 Hz,

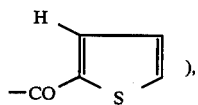),

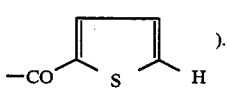).

mass (EI/DI) m/e: 287 (M+), 73 (base peak).

EXAMPLE 7

N-acetyl-2-[[2-(trimethylsilyl)ethyl]thio]ethyl amine

This compound is prepared by the similar procedure as in the case of EXAMPLE 1, except for the treatment with 1.97 g (25.0 mmol) of acetyl chloride instead of benzoyl chloride.

Yield: 5.08 g (92.8%).
b.p.: 187° C. (1 mm).
Anal. Calcd. for: $C_9H_{21}NOSSi$. C 49.27; H 0.65; N 6.38. Found: C 48.67; H 9.81; N 6.55.
IR: $\nu_{max}^{CHCl_3}$ cm$^{-1}$: 3460 ($\nu_{NH}$), 3010, 2970 ($\nu_{CH}$), 1670 ($\nu_{C=O}$), 1515 ($\delta_{NH}$), 1215 ($\nu_{C-Si}$).
$^1$H-NMR(CDCl$_3$)δ: 0.01 (9H, s, —Si(CH$_3$)$_3$) 0.85 (2H, A$_2$B$_2$,

), 1.97 (3H, s, CH$_3$CO—), 2.55 (2H, A$_2$B$_2$,

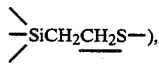), 2.65 (2H, t, J=6 Hz, —SCH$_2$CH$_2$N—), 3.41 (2H, q, J=6 Hz, —CH$_2$NHCO—), 6.12 (1H, m, —NHCO—).
mass (EI/DI) m/e: 219 (M+), 73 (base peak)

EXAMPLE 8

N-cyclohexanecarbonyl-2-[[2-(trimethylsilyl)ethyl]thio]ethyl amine

This compound is prepared by the similar procedure as in the case of EXAMPLE 1, except for the treatment with 3.67 g (25.0 mmol) of cyclohexanecarboxylic acid chloride instead of benzoyl chloride.

Yield: 6.50 g (90.6%).
b.p.: 240° C. (1 mm).
Anal. Calcd. for: $C_{14}H_{29}NOSSi$. C 58.48; H 10.17; N 4.87. Found: C 57.97; H 10.39; N 5.09.
IR: $\nu_{max}^{neat}$cm$^{-1}$: 3320 ($\nu_{NH}$), 2940, 2860 ($\nu_{CH}$), 1645 ($\nu_{C=O}$), 1545 ($\delta_{NH}$), 1250 ($\nu_{C-Si}$).

$^1$H-NMR(CDCl$_3$)δ: 0.01 (9H, s, —Si(CH$_3$)$_3$), 0.84 (2H, A$_2$B$_2$,

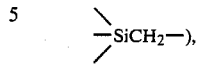), 1.0–2.3 (11 Hz, m, H of cyclohexyl), 2.55 (2H, A$_2$B$_2$,

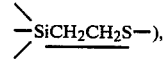), 2.63 (2H, t, J=6 Hz, —SCH$_2$CH$_2$N—) 3.41 (2H, q, J=6 Hz, —CH$_2$NHCO—), 5.97 (1H, m, —NHCO—).
mass (EI/DI) m/e: 287 (M+), 73 (base peak).

EXAMPLE 9

N-octanoyl-2-[[2-(trimethylsilyl)ethyl]thio]ethyl amine

This compound is prepared by the similar procedure as in the case of EXAMPLE 1, except for the treatment with 4.07 g (25.0 mmol) of octanoyl chloride instead of benzoyl chloride.

Yield: 6.80 g (89.8%).
b.p.: 228° C. (1 mm).
Anal. Calcd. for: $C_{15}H_{33}NOSSi$. C 59.35; H 10.96; N 4.61. Found: C 58.97; H 11.21; N 4.62.
IR: $\nu_{max}^{CHCl_3}$ cm$^{-1}$: 3460 ($\nu_{NH}$), 2960, 2940, 2860 ($\nu_{CH}$), 1665 ($\nu_{C=O}$), 1510 ($\delta_{NH}$), 1250 ($\nu_{C-Si}$).
$^1$H-NMR(CDCl$_3$)δ: 0.01 (9H, s, —Si(CH$_3$)$_3$), 0.84 (2H, A$_2$B$_2$,

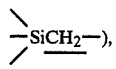), 0.85 (3H, t, J=6.5 Hz, —(CH$_2$)$_6$CH$_3$), 1.0–1.8 (10H, m), 2.17 (2H, t, J=6.5 Hz, —NHCO—CH$_2$—), 2.55 (2H, A$_2$B$_2$,

2.65 (2H, t, J=6 Hz, —SCH$_2$CH$_2$N—), 3.41 (2H, q, J=6 Hz, —CH$_2$NHCO—), 5.96 (1H, m, —NHCO—).
mas (EI/DI) m/e: 303 (M+), 73 (base peak).

EXAMPLE 10

N-(p-toluenesulfonyl)-2-[[2-(trimethylsilyl)ethyl]thio]ethyl amine

This compound is prepared by the similar procedure as in the case of EXAMPLE 1, except for the treatment with 4.77 g (25.0 mmol) of p-toluenesulfonyl chloride instead of benzoyl chloride.

Yield: 7.70 g (93.1%).
b.p.: 279° C. (1 mm).
Anal. Calcd. for: $C_{14}H_{25}NO_2SSi$. C 50.71; H 7.60; N 4.22. Found: C 50.28; H 7.80; N 4.34.
IR: $\nu_{max}^{neat}$cm$^{-1}$: 3300 ($\nu_{NH}$), 2960, 2920 ($\nu_{CH}$), 1600 ($\nu_{arom.}$), 1500 ($\nu_{arom.}$), 1415 ($\nu_{SO_2}$), 1250 ($\nu_{C-Si}$), 1160 ($\nu_{SO_2}$).

$^1$H-NMR(CDCl$_3$)δ: 0.01 (9H, s, —Si(CH$_3$)$_3$), 0.78 (2H, A$_2$B$_2$,

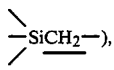

2.42 (2H, A$_2$B$_2$,

2.43 (3H, s, arom.CH$_3$), 2.60 (2H, t, J=6 Hz, —SCH$_2$CH$_2$N—), 3.11 (2H, q, J=6 Hz, —CH$_2$NHSO$_2$—), 5.13 (1H, t, J=6 Hz, —NHSO$_2$—), 7.30 (2H, d, J=8 Hz, arom.H), 7.76 (2H, d, J=8 Hz, arom.H).

mass (EI/DI) m/e: 331 (M$^+$), 73 (base peak).

EXAMPLE 11

N-methanesulfonyl-2-[[2-(trimethylsilyl)ethyl]thio]ethyl amine

This compound is prepared by the similar procedure as in the case of EXAMPLE 1, except for the treatment with 2.85 g (25.0 mmol) of methanesulfonyl chloride instead of benzoyl chloride.

Yield: 5.77 g (90.5%).
m.p.: 41°–41° C.
Anal. Calcd. for: C$_8$H$_{21}$NO$_2$S$_2$Si. C 37.61; H 8.29; N 5.48. Found: C 37.30; H 8.55; N 5.48.
IR: $\nu_{max}^{KBr}$cm$^{-1}$: 3280 ($\nu_{NH}$), 1410, 1150 ($\nu_{SO_2}$) 1250 ($\nu_{C-Si}$).
$^1$H-NMR(CDCl$_3$)δ: 0.00 (9H, s, —Si(CH$_3$)$_3$), 0.81 (2H, A$_2$B$_2$,

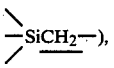

2.52 (2H, A$_2$B$_2$,

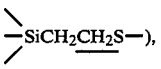

2.68 (2H, t, J=6 Hz, —SCH$_2$CH$_2$N—), 2.93 (3H, s, —NHSO$_2$CH$_3$), 3.25 (2H, q, J=6 Hz, —SCH$_2$CH$_2$N—) 5.03 (1H, t, J=6 Hz, —NHSO$_2$—).

mass (EI/DI) m/e: 255 (M$^+$), 73 (base peak).

EXAMPLE 12

N-formyl-2-[[2-(trimethylsilyl)ethyl]thio]ethyl amine

To a solution of 0.500 g (2.80 mmol) of 2-[[2-(trimethylsilyl)ethyl]thio]ethyl amine in 6.30 g (0.140 mol) of 98% formic acid, 2.10 g (20.0 mmol) of acetic acid is added dropwise at 0°–5° C.

The mixture is stirred at 0°–5° C. for 30 min, and then at 25° C. for 1 hr.

The reaction mixture is neutralized with a dilute aqueous ammonia, and extracted with diethyl ether, the extract is washed with water, dried over sodium sulfate, and then evaporated in vacuo.

The resulting oily residue is distilled to afford N-formyl-2-[[2-(trimethylsilyl)ethyl]thio]ethyl amine (0.550 g, 95.0%).

IR: $\nu_{max}^{CHCl_3}$(cm$^{-1}$): 3455 ($\nu_{NH}$), 2970 ($\nu_{CH}$), 1690 ($\nu_{C=O}$), 1505 ($\delta_{NH}$), 1250 ($\nu_{C-Si}$).
$^1$H-NMR(CDCl$_3$)δ: 0.01 (9H, s, (CH$_3$)$_3$Si—) 0.83 (2H, A$_2$B$_2$,

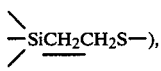

2.56 (2H, A$_2$B$_2$,

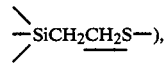

2.70 (2H, t, J=6 Hz, —SCH$_2$CH$_2$NH—), 3.52 (2H, q, J=6 Hz, —CH$_2$NHCO—), 8.17 (1H, brs, —NHCO—).

mass (EI/DI) m/e: 205 (M$^+$), 73 (base peak).

EXAMPLE 13

N-methyl-2-[[2-(trimethylsilyl)ethyl]thio]ethyl amine

A solution of 400 mg (2.00 mmol) of N-formyl-2-[[2-(trimethylsilyl)ethyl]thio]ethyl amine in 5 ml of absolute diethyl ether is added under argon at 0° C. to a stirred slurry of 152 mg (4.00 mmol) of lithium aluminum hydride in 5 ml of the same solvent. After 1 hr at 20° C., the stirred reaction mixture is quenched by addition of 0.6 ml of water and 0.15 ml of 15% sodium hydroxide solution, the resulting precipitate is filtered off, washed with diethyl ether. The combined organic layers is evaporated in vacuo, and the residue is distilled to N-methyl-2-[[2-(trimethylsilyl)ethyl]thio]ethyl amine (350 mg, 93.5%).

b.p.: 125° C. (8 mm).
Anal. Calcd. for: C$_8$H$_{21}$NSSi. C 50.20; H 11.06; N 7.32. Found: C 49.91; H 11.15; N 7.05.
IR: $\nu_{max}^{CHCl_3}$(cm$^{-1}$): 3300 ($\nu_{NH}$), 2970, 2930, 2810 ($\nu_{CH}$), 1260 ($\nu_{C-Si}$).
$^1$H—NMR(CDCl$_3$)δ: 0.03 (9H, s, (CH$_3$)$_3$Si—), 0.84 (2H, A$_2$B$_2$,

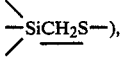

1.54 (1H, s, —NH—), 2.43 (3H, s, —NHCH$_3$), 2.53 (2H, A$_2$B$_2$,

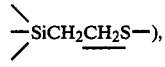

2.70 (4H, A$_2$B$_2$, —SCH$_2$CH$_2$N).

mass (EI/GC) m/e: 191 (M$^+$), 91 (base peak)

EXAMPLE 14

N-methyl-2-[[2-(trimethylsilyl)ethyl]thio]ethyl amine maleate 3.00 g (15.7 mmol) of N-methyl-2-[[2-(trimethylsilyl)ethyl]thio]ethyl amine is added dropwise to a solution of 1.82 g (15.7 mmol) of maleic acid in 10 ml acetone.

To the reaction mixture, 40 ml of diethyl ether is added and left to stand at room temperature.

The crystals is filtered, and washed with diethyl ether and dried to afford N-methyl-2-[[2-(trimethylsilyl)ethyl]thio]ethyl amine maleate (4.30 g, 89.4%).

m.p.: 90°–92° C.

Anal. Calcd. for: $C_8H_{21}NSSi \cdot C_4H_4O_4$. C 46.87; H 8.20; N 4.56. Found: C 46.58; H 8.44; N 4.56.

IR: $\nu_{max}^{KBr}$ cm$^{-1}$: 3440 ($\nu_{CH}$), 2970, 2920 ($\nu_{CH}$), 2750 ($\nu_{NH_2^{\oplus}}$) 1620 ($\nu_{COO^{\ominus}}$), 1250 ($\nu_{C-Si}$).

$^1$H-NMR (CD$_3$OD)δ: 0.04 (9H, s, —Si(CH$_3$)$_3$), 0.87 (2H, A$_2$B$_2$,

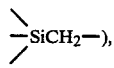

2.64 (2H, A$_2$B$_2$,

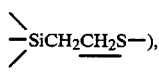

2.73 (3H, s, —NHCH$_3$), 2.83 (2H, A$_2$B$_2$, SCH$_2$CH$_2$NH—), 3.20 (2H, A$_2$B$_2$, SCH$_2$CH$_2$NH—), 6.26 (2H, s, maleic acid).

mass (EI/GC) m/e: 191 (M+), 92 (base peak). (Free base).

EXAMPLE 15

N-trifluoroacetyl-2-[[2-(trimethylsilyl)ethyl]thio]ethyl amine

To a solution of 3.54 g (20.0 mmol) of 2-[[2-(trimethylsilyl)ethyl]thio]ethyl amine in 10 ml of absolute pyridine, 8.40 g (40.0 mmol) of trifluoroacetic anhydride is added dropwise under argon at 0° C., and then stirred for 7 hrs at 20° C.

The reaction mixture is poured into water, neutralized with concentrated hydrochloric acid, and extracted with diethyl ether. The combined organic layers is washed with water, dried over sodium sulfate, and then evaporated in vacuo. The residue is distilled to afford N-trifluoroacetyl-2-[[2-(trimethylsilyl)ethyl]thio]ethyl amine (5.00 g, 90.9%).

b.p.: 170° C. (2 mm)

Anal. Calcd. for: $C_9H_{18}F_3NOSSi$. C 39.54; H 6.64; N 5.12. Found: C 39.26; H 6.85; N 5.29.

IR: $\nu_{max}^{CDCl_3}$(cm$^{-1}$): 3460 ($\nu_{NH}$), 2980 ($\nu_{CH}$), 1730 ($\nu_{C=O}$), 1540 ($\delta_{NH}$), 1260 ($\nu_{C-Si}$), 1170 ($\nu_{C-F}$).

$^1$H-NMR(CDCl$_3$)δ: 0.01 (9H, s, (CH$_3$)$_3$Si—), 0.82 (2H, A$_2$B$_2$,

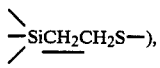

2.55 (2H, A$_2$B$_2$,

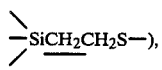

2.71 (2H, t, J=6 Hz, —SCH$_2$CH$_2$N—), 3.52 (2H, q, J=6 Hz, —CH$_2$NHCO—), 6.88 (1H, brs, —NHCO—).

mass (EI/DI) m/e: 273 (M+), 73 (base peak).

EXAMPLE 16

N-allyl-N-trifluoroacetyl-2-[[2-(trimethylsilyl)ethyl]thio]ethyl amine 115 mg (4.80 mmol) of sodium hydride, freed from protective mineral oil by three 3-ml n-hexane washings, is added to 6 ml of absolute tetrahydrofuran under argon at 0°–5° C. The addition of 1.10 g (4.00 mmol) of N-trifluoroacetyl-2-[[2-(trimethylsilyl)ethyl]thio]ethyl amine to the stirred suspension is attended by vigorous gas (H$_2$) evolution. After 5 min, 5 mg of 18-crown-6 and 678 mg (5.60 mmol) of freshly distilled allyl bromide are added, and then at reflux temperature for 12 hrs.

Tetrahydrofuran is removed by evaporation in vacuo, the residue is dissolved in diethyl ether, washed with a dilute hydrochloric acid solution and water, the organic layer is dried over sodium sulfate, and then evaporated in vacuo.

The oily residue is distilled to afford N-allyl-N-trifluoroacetyl-2-[[2-(trimethylsilyl)ethyl]thio]ethyl amine (1.10 g, 87.3%).

b.p.: 140° C. (1 mm).

Anal. Calcd. for: $C_{12}H_{22}F_3NOSSi$. C 45.98; H 7.07; N 4.47. Found: C 46.23; H 7.34; N 4.62.

IR: $\nu_{max}^{CDCl_3}$(cm$^{-1}$): 2960 ($\nu_{CH}$), 1690 ($\nu_{C=O}$), 1250 ($\nu_{C-Si}$), 1150 ($\nu_{C-F}$).

$^1$H-NMR (CDCl$_3$)δ: 0.01 (9H, s, (CH$_3$)$_3$Si—), 0.84 (2H, A$_2$B$_2$,

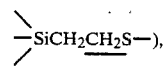

2.62 (4H, m, —CH$_2$SCH$_2$—), 3.53 (2H, t, J=6 Hz, —SCH$_2$CH$_2$N—), 4.05 (2H, d, J=6 Hz, —NCH$_2$CH=CH$_2$), 5.0–5.3 (2H, m, —CH$_2$CH=CH$_2$), 5.6–6.0 (1H, m, —CH$_2$CH=CH$_2$).

mass (EI/DI) m/e: 313 (M+).

EXAMPLE 17

N-allyl-2-[[2-(trimethylsilyl)ethyl]thio]ethyl amine

A mixture of 500 mg (1.60 mmol) of N-allyl-N-trifluoroacetyl-2-[[2-(trimethylsilyl)ethyl]thio]ethyl amine and 180 mg (3.20 mmol) of potassium hydroxide in methanol is stirred at 20° C. for 2 hrs.

Most of the methanol is removed by evaporation in vacuo, the residue is dissolved in diethyl ether, washed with water, the organic layer is dried over sodium sulfate, and then evaporated in vacuo.

The oily residue is distilled to afford N-allyl-2-[[2-(trimethylsilyl)ethyl]thio]ethyl amine (280 mg, 80.6%).

b.p.: 110° C. (2 mm).

Anal. Calcd. for: $C_{10}H_{23}NSSi$. C 55.24; H 10.66; N 6.44. Found: C 55.46; H 10.86; N 6.56.

IR: $\nu_{max}^{CHCl_3}$(cm$^{-1}$): 3300 ($\nu_{NH}$), 2960, 2925 ($\nu_{CH}$) 1450 ($\delta_{CH}$), 1250 ($\nu_{C-Si}$).

$^1$H-NMR (CDCl$_3$)δ: 0.01 (9H, s, (CH$_3$)$_3$Si—), 0.84 (2H, A$_2$B$_2$,

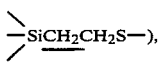

1.51 (1H, s, —NH—), 2.54 (2H, A$_2$B$_2$,

2.73 (4H, A$_2$B$_2$, —CH$_2$SCH$_2$—), 3.25 (2H, dt, T=6 Hz, 1 Hz, NH—CH$_2$CH=CH$_2$), 5.08 (1H, m,

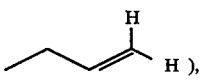

5.14 (1H, m,

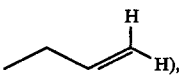

5.90 (1H, m, —CH=CH$_2$).

mass (EI/GC) m/e: 217 (M+), 70 (base peak).

EXAMPLE 18

N-allyl-2-[[2-(trimethylsilyl)ethyl]thio]ethyl amine maleate 5.30 g (24.4 mmol) of N-allyl-2-[[2-(trimethylsilyl)ethyl]thio]ethyl amine is added dropwise to a solution of 2.83 g (24.4 mmol) of maleic acid in 15 ml of acetone.

The reaction mixture is concentrated to one-third and then 50 ml of diethyl ether is added, and left to stand at room temperature.

The resulting crystals is filtered, washed with diethyl ether, and dried to afford N-allyl-2-[[2-(trimethylsilyl)ethyl]thio]ethyl amine maleate (6.90 g, 87.7%).

m.p.: 93°–94° C.

Anal. Calcd. for: C$_{10}$H$_{23}$NSSi.C$_4$H$_4$O$_4$. C 50.42; H 8.16; N 4.20. Found: C 50.13; H 8.44; N 4.24.

IR: $\nu_{max}^{KBr}$cm$^{-1}$: 3440 ($\nu_{OH}$), 2960, 2860 ($\nu_{CH}$) 2800 ($\nu_{NH2}{}^{\ominus}$), 1620 ($\nu_{C=C}$), 1580 ($\nu_{COO}{}^{\ominus}$), 1245 ($\nu_{C-Si}$).

$^1$H-NMR (CD$_3$OD)δ: 0.04 (9H, s, Si(CH$_3$)$_3$), 0.87 (2H, A$_2$B$_2$,

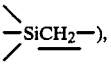

2.64 (2H, A$_2$B$_2$,

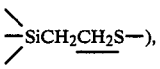

2.83 (2H, A$_2$B$_2$, —SCH$_2$CH$_2$N—), 3.21 (2H, A$_2$B$_2$, —SCH$_2$CH$_2$N—), 3.70 (2H, d, J=6 Hz, NHCH$_2$CH=CH$_2$), 5.48 (1H, d, J=12 Hz,

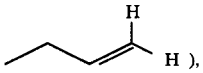

5.53 (1H, d, J=16 Hz,

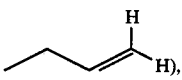

5.95 (1H, m, —CH$_2$CH=CH$_2$), 6.26 (2H, s, maleic acid).

mass (EI/GC) m/e: 217 (M+), 70 (base peak).

EXAMPLE 19

N-cyclohexyl-2-[[2-(trimethylsilyl)ethyl]thio]ethyl amine

To a solution of 500 mg (2.80 mmol) of 2-[[2-(trimethylsilyl)ethyl]thio]ethyl amine in 10 ml of absolute methanol is added 0.40 ml (2.00 mmol) of 5N HCl-methanol, followed by 277 mg (2.80 mmol) of cyclohexanone and 100 mg (1.60 mmol) of sodium cyanohydridoborate (NaBH$_3$CN).

The solution is stirred at 25° C. for 48 hrs, then the reaction mixture is poured into 15 ml of water, extracted with diethyl ether. The aqueous solution is brought to pH>10 with aqueous ammonia, extracted with two 10-ml portions of diethyl ether. The combined extracts is dried over sodium sulfate, and evaporated in vacuo to dryness. The oily residue is distilled to afford N-cyclohexyl-2-[[2-(trimethylsilyl)ethyl]thio]ethyl amine (260 mg, 35.5%).

b.p.: 170° C. (1 mm).

Anal. Calcd. for: C$_{13}$H$_{29}$NSSi. C 60.16; H 11.26; N 5.40. Found: C 59.87; H 11.46; N 5.33.

IR: $\nu_{max}^{CHCl_3}$(cm$^{-1}$): 3200 ($\nu_{NH}$), 2950, 2860 ($\nu_{CH_2}$) 1450 ($\delta_{CH_2}$), 1250 ($\nu_{C-Si}$).

$^1$H-NMR (CDCl$_3$)δ: 0.03 (9H, s, (CH$_3$)$_3$Si—), 0.84 (2H, A$_2$B$_2$,

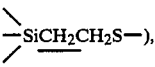

1.0–2.0 (10H, m, —CH$_2$—), 2.53 (2H, A$_2$B$_2$,

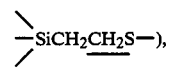

2.55 (2H, A$_2$B$_2$, —SCH$_2$CH$_2$NH$_2$), 2.90 (2H, A$_2$B$_2$, —SCH$_2$CH$_2$NH$_2$).

mass (EI/GC) m/e: 259 (M+), 116 (base peak).

EXAMPLE 20

N-cyclohexyl-2-[[2-(trimethylsilyl)ethyl]thio]ethyl amine maleate 4.00 g (15.4 mmol) of N-cyclohexyl-2-[[2-(trimethylsilyl)ethyl]thio]ethyl amine is added dropwise to a solution of 1.79 g (15.4 mmol) of maleic acid in 20 ml of acetone, and left to stand at room temperature.

The resulting crystals is filtered, washed with diethyl ether and dried to afford N-cyclohexyl-2-[[2-(trimethylsilyl)ethyl]thio]ethyl amine maleate (5.49 g, 94.8%).

m.p.: 134°–135° C.
Anal. Calcd. for: $C_{13}H_{29}NSSi \cdot C_4H_4O_4$. C 54.36; H 8.86; N 3.73. Found: C 54.14; H 9.06; N 3.74.
IR: $\nu_{max}^{KBr}$cm$^{-1}$: 3440 ($\nu_{OH}$), 2950, 2860 ($\nu_{CH}$) 2770 ($\nu_{NH_2\oplus}$), 1620 ($\nu_{C=C}$), 1580 ($\nu_{COO\ominus}$), 1245 ($\nu_{C-Si}$).
$^1$H-NMR (CD$_3$OD)δ: 0.04 (9H, s, —Si(CH$_3$)$_3$), 0.87 (2H, A$_2$B$_2$, $\diagdown$
—SiCH$_2$—),
$\diagup$ 1.0–2.3 (10H, m, —CH$_2$—), 2.65 (2H, A$_2$B$_2$, $\diagdown$
—SiCH$_2$CH$_2$S—),
$\diagup$ 2.81 (2H, A$_2$B$_2$, —SCH$_2$CH$_2$N—), 3.22 (2H, A$_2$B$_2$, —SCH$_2$CH$_2$N—), 6.25 (2H, s, maleic acid).

| Compd. No. | Formula |
|---|---|
| SKK-009 | (H$_3$C)$_3$Si—CH$_2$CH$_2$S—CH$_2$CH$_2$NHCH$_3$ · maleic acid |
| SKK-010 | (H$_3$C)$_3$Si—CH$_2$CH$_2$—S—CH$_2$CH$_2$NH—(cyclohexyl) · maleic acid |
| SKK-011 | (H$_3$C)$_3$Si—CH$_2$CH$_2$—S—CH$_2$CH$_2$NHCH$_2$—CH=CH$_2$ · maleic acid |
| SKK-012 | (H$_3$C)$_3$Si—CH$_2$CH$_2$—S—CH$_2$CH$_2$—NH—C(=O)—C$_6$H$_5$ |
| SKK-020 | (H$_3$C)$_3$Si—CH$_2$CH$_2$—S—CH$_2$CH$_2$NH—C(=O)—C$_6$H$_4$—Cl |
| SKK-021 | (H$_3$C)$_3$Si—CH$_2$CH$_2$—S—CH$_2$CH$_2$NH—C(=O)—(3-pyridyl) |
| SKK-022 | (H$_3$C)$_3$Si—CH$_2$CH$_2$—S—CH$_2$CH$_2$NH—C(=O)—(2-furyl) |
| SKK-023 | (H$_3$C)$_3$Si—CH$_2$CH$_2$—S—CH$_2$CH$_2$—NH—C(=O)—(2-thienyl) |
| SKK-024 | (H$_3$C)$_3$Si—CH$_2$CH$_2$—S—CH$_2$CH$_2$—NH—C(=O)—(1-naphthyl) |
| SKK-025 | (H$_3$C)$_3$Si—CH$_2$CH$_2$—S—CH$_2$CH$_2$—NH—C(=O)—CH$_3$ |

-continued

| Compd. No. | Formula |
|---|---|
| SKK-026 | $(H_3C)_3Si-CH_2CH_2-S-CH_2CH_2-NH-C(=O)-C_6H_{11}$ |
| SKK-027 | $(H_3C)_3Si-CH_2CH_2-S-CH_2CH_2-NH-C(=O)-(CH_2)_6CH_3$ |
| SKK-028 | $(H_3C)_3Si-CH_2CH_2-S-CH_2CH_2NHSO_2-C_6H_4-CH_3$ |
| SKK-029 | $(H_3C)_3Si-CH_2CH_2-S-CH_2CH_2NHSO_2-CH_3$ |

TESTS ON PHARMACEUTICAL EFFECTS

Test 1 (proliferation inhibiting effect in explantation)

Following carcinomata are employed.
(1) Lewis lung carcinoma (hereinafter referred to as "LLC"),
(2) Ehrlich ascites carcinoma (hereinafter referred to as "EAC"),
(3) K.B. carcinoma (hereinafter referred to as "KB"), and
(4) B-16 melanoma carcinoma (hereinafter referred to as "B-16").

$1 \times 10^5$ cells of each carcinoma are cultured for 24 hours in an ox serum eagle culture solution with use of a culture test tube and a carbon dioxide gas culturing device (5% $CO_2$, 37° C.). After 24 hours, the used culture solution was flowed-out and each 0.1 ml of a freshly prepared culture solution containing a compound according to the invention was added to further continue the culture for 3 days. After completion of the culture, number of living cells was measured with use of a dye-exclusion method due to tripan blue dying. To each of control groups, 0.1 ml of the same culture solution but containing no compound according to the invention was added.

Concentrations on 50% inhibition of the carcinoma cells ($IC_{50}$) were determined between the testing groups and control groups, according to the manner as stated above. Results are shown in following Table.

| Compound No. | $IC_{50}$ (μg/ml) | | | |
|---|---|---|---|---|
| | LLC | EAC | KB | B-16 |
| SKK-012 | 4.3 | 15 | 17 | 16 |
| SKK-021 | 5 | 12 | 10 | <5 |
| SKK-022 | 9 | 15 | 17 | 20 |
| SKK-024 | 13 | 18 | 14 | 25 |
| SKK-028 | 14 | 30 | 10 | 14 |

Test 2 (carcinoma cell weight inhibiting effect in mice)

B-16 and EAC were given to BDF and ICR-CD mice, respectively by a hypodermic injection. $1.0 \times 10^5$ cells on B-16 and $5.0 \times 10^6$ cells on EAC were given to each mouse. Each of the compounds according to the invention was orally dosed for 5 days in an amount of 1/5 $LD_{50}$ (one time/day). After lapsed 21 days from the final dosage, the carcinoma of each mouse was exenterated, measured its weight and calculated a mean weight as the inhibiting ratio which is shown in the following Table.

| Compound No. | Name of Carcinomata | |
|---|---|---|
| | B-16 | EAC |
| SKK-012 | 62 | 76 (inhibiting ratio) |
| SKK-021 | 93 | 70 |
| SKK-022 | 58 | 65 |
| SKK-024 | 60 | 62 |
| SKK-028 | 85 | 55 |

Test 3 (acute toxicity)

Each of compounds according to the invention was suspended in 0.1% P-1570 aqueous solution of sugar ester or 0.5% CMC aqueous solution. The suspension abdominally or orally dosed to ICR female mice (weight: 20±1 g). The tested mice were observed for 7 days and $LD_{50}$ was determined based on Lichfield-Wilcoxon method. Results were shown in following Table.

| Compound No. | Acute Toxicity ($LD_{50}$, mg/kg) | |
|---|---|---|
| | Abdominal Dosage | Oral Dosage |
| SKK-009 | 189 | 800 |
| SKK-010 | 152 | 825 |
| SKK-011 | 134 | 846 |
| SKK-012 | 1190 | >2000 |
| SKK-021 | <500 | >2000 |
| SKK-022 | <1000 | >2000 |
| SKK-023 | >1000 | >2000 |
| SKK-024 | >2000 | >3000 |
| SKK-025 | ±100 | 1000–2000 |
| SKK-026 | 500–1000 | 1000–2000 |
| SKK-027 | 2000–3000 | >3000 |
| SKK-028 | >2500 | >3000 |

EXAMPLES FOR THE PREPARATION OF MEDICINES

Example 1 (tablet)

Tablets were prepared in a conventional manner with use of following components.

| | |
|---|---|
| Compound (SKK-012) | 100 (mg) |
| Crystallized cellulose | 20 |
| Lactose | 41 |
| Corn starch | 30 |
| Hydroxypropyl cellulose | 6 |
| Magnesium stearate | 3 |
| | 200 mg/tablet |

Example 2 (capsule)

Following components were mixed and sealed in a capsule with use of a conventional manner.

| | |
|---|---|
| Compound (SKK-022) | 200 (mg) |
| Crystallized cellulose | 50 |
| Silicic anhydride | 2 |
| Magnesium stearate | 3 |
| | 255 mg/capsule |

Example 3 (granule)

Granules were prepared in a conventional manner with use of following components and individually packed in aluminum foil bag.

| | |
|---|---|
| Compound (SKK-021) | 500 (mg) |
| Lactose | 323 |
| Corn starch | 150 |
| Polyvinyl-pyrrolidon | 25 |
| Silicic anhydride | 2 |
| | 1000 mg/package |

Example 4 (suppository)

Suppositories were prepared by mixing following components and moulding the same.

| | |
|---|---|
| Compound (SKK-028) | 300 (mg) |
| Witepsol W-35 | 1700 |
| | 2000 mg/suppository |

Example 5 (injection)

A solution for injectional dosage was prepared by mixing following components and sealed in a glass ampule in a conventional manner.

| | |
|---|---|
| Compound (SKK-009) | 25 (mg) |
| Sodium chloride | 25 |
| Distilled water for injection | suitable amount |
| | 10 ml/ampule |

We claim:

1. A novel organosilicon compound represented by a formula

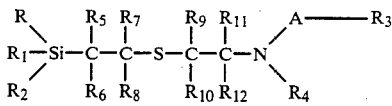

wherein A is methylene, carbonyl or sulfonyl, R, $R_1$ and $R_2$ are alkyl of 1 to 7 carbon atoms, respectively, $R_3$ is hydrogen, alkyl of 1 to 7 carbon atoms, alkyl of 1 to 7 carbon atoms substituted with halogen, alkenyl of 2 to 7 carbon atoms, phenyl, phenyl substituted with chloro, bromo, methyl or methoxy, naphthyl, naphthyl substituted with —OH or methoxy, pyridyl, cyclohexyl methyl substituted pyridyl, furyl, methyl substituted furyl, thienyl, methyl substituted thienyl or cycloalkyl when taken together with substituent A; $R_4$ is hydrogen, alkyl of 1 to 7 carbon atoms or alkenyl of 2 to 7 carbon atoms; and $R_5$, $R_6$, $R_7$, $R_8$, $R_9$, $R_{10}$, $R_{11}$ and $R_{12}$ are hydrogen, or a non-toxic, salt thereof with the provision that $R_4$ is not alkyl when A is methylene and $R_3$ is hydrogen.

2. A salt of the organosilicon compound as claimed in claim 1, wherein said non-toxic salt is maleate.

3. An organosilicon compound as claimed in claim 1, wherein R, $R_1$ and $R_2$ are methyl group, respectively and $R_5$, $R_6$, $R_7$, $R_8$, $R_9$, $R_{10}$, $R_{11}$ and $R_{12}$ are hydrogen, respectively, or a non-toxic salt thereof.

4. A salt of the organosilicon compound as claimed in claim 3, wherein said non-toxic salt is maleate.

5. An organosilicon compound as claimed in claim 1, wherein R, $R_1$ and $R_2$ are methyl group, respectively, $R_5$, $R_6$, $R_7$, $R_8$, $R_9$, $R_{10}$, $R_{11}$ and $R_{12}$ are hydrogen, respectively and A is carbonyl group.

6. An organosilicon compound as claimed in claim 1, wherein R, $R_1$ and $R_2$ are methyl group, respectively, $R_5$, $R_6$, $R_7$, $R_8$, $R_9$, $R_{10}$, $R_{11}$ and $R_{12}$ are hydrogen, respectively and A is sulfonyl group.

7. An organosilicon compound as claimed in claim 1, wherein R, $R_1$ and $R_2$ are methyl group, respectively, $R_5$, $R_6$, $R_7$, $R_8$, $R_9$, $R_{10}$, $R_{11}$ and $R_{12}$ are hydrogen, respectively and -A-$R_3$ is alkenyl group, or a non-toxic salt thereof.

8. An organosilicon compound as claimed in claim 1, wherein R, $R_1$ and $R_2$ are methyl group, respectively, $R_5$, $R_6$, $R_7$, $R_8$, $R_9$, $R_{10}$, $R_{11}$ and $R_{12}$ are hydrogen, respectively and -A-$R_3$ is cycloalkyl group, or a non-toxic salt thereof.

9. An antitumor composition comprising an antitiumor effective amount of at least one compound of claim 1 and a pharmaceutical carrier.

10. An antitumor composition as claimed in claim 9, wherein said effective component is N-benzoyl-2-[(2-trimethylsilylethyl)thio]ethylamine.

11. An antitumor composition as claimed in claim 9, wherein said effective component is N-(p-chlorobenzoyl)-2-[(2-trimethylsilylethyl)thio]ethylamine.

12. An antitumor composition as claimed in claim 9, wherein said effective component is N-(1-naphthoyl)-2-[(2-trimethylsilylethyl)thio]ethylamine.

13. An antitumor composition as claimed in claim 9, wherein said effective component is N-nicotinoyl-2-[(2-trimethylsilylethyl)thio]ethylamine.

14. An antitumor composition as claimed in claim 9, wherein said effective component is N-(2'-furoyl)-2-[(2-trimethylsilylethyl)thio]ethylamine.

15. An antitumor composition as claimed in claim 9, wherein said effective component is N-thenoyl-2-[(2-trimethylsilylethyl)thio]ethylamine.

16. An antitumor composition as claimed in claim 9, wherein said effective component is N-acetyl-2-[(2-trimethylsilylethyl)thio]ethylamine.

17. An antitumor composition as claimed in claim 9, wherein said effective component is N-cyclohexylcarbonyl-2-[(2-trimethylsilylethyl)thio]ethylamine.

18. An antitumor composition as claimed in claim 9, wherein said effective component is N-octanoyl-2-[(2-trimethylsilylethyl)thio]ethylamine.

19. An antitumor composition as claimed in claim 9, wherein said effective component is N-(p-toluenesulfonyl)-2-[(2-trimethylsilylethyl)thio]ethylamine.

20. An antitumor composition as claimed in claim 9, wherein said effective component is a maleate of N-methyl-2-[(2-trimethylsilylethyl)thio]ethylamine.

21. An antitumor composition as claimed in claim 9, wherein said effective component is maleate of N-allyl-2-[(2-trimethylsilylethyl)thio]ethylamine.

22. An antitumor composition as claimed in claim 9, wherein said effective component is maleate of N-cyclohexyl-2-[(2-trimethylsilylethyl)thio]ethylamine.

* * * * *

UNITED STATES PATENT AND TRADEMARK OFFICE
CERTIFICATE OF CORRECTION

PATENT NO. : 4,560,679
DATED : Dec. 24, 1985
INVENTOR(S) : SHIGESHI TOYOSHIMA, RYOICHI UNNO, and KOICHI ITO It is certified that error appears in the above-identified patent and that said Letters Patent are hereby corrected as shown below:

| Col. | Line | Abstract | | | |
|---|---|---|---|---|---|
| [57] | | 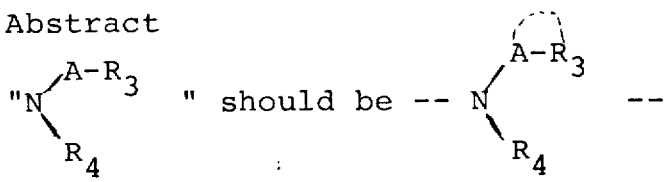 | | | |
| 1 | 30 | " " " " " " " " " " " " " " " | | | |
| 5 | 33 | Example 1 | "-SCH$_2$CH$_2$N-)" | should be | --SCH$_2$CH$_2$N-)-- |
| 5 | 34 | " " | "-CH$_2$NHCO-)" | " " | --CH$_2$NHCO-)-- |
| 6 | 1 | Example 2 | "-SCH$_2$CH$_2$N-)" | " " | --SCH$_2$CH$_2$N-) |
| 6 | 2 | " " | "-CH$_2$NHCO-)" | " " | --CH$_2$NHCO-)-- |
| 6 | 25 | " 3 | Left Out After | "0.85" | --(2H, A$_2$B$_2$- -- |
| 6 | 30 | " " ". " " | " | "2.63" | -- " " " " " " |
| 6 | 37 | Example 3 | "-SCH$_2$CH$_2$N-)" | should be | --SCH$_2$CH$_2$N-)-- |
| 6 | 38 | " " | "-CH$_2$NHCO-)" | " " | --CH$_2$NHCO-)-- |
| 7 | 8 | Example 4 | "SCH$_2$CN$_2$N-)" | " " | --SCH$_2$CH$_2$N-)-- |
| 7 | 15 | |  | | |

UNITED STATES PATENT AND TRADEMARK OFFICE
CERTIFICATE OF CORRECTION

PATENT NO. : 4,560,679

DATED : Dec. 24, 1985

INVENTOR(S) : SHIGESHI TOYOSHIMA, RYOICHI UNNO, and KOICHI ITO

It is certified that error appears in the above-identified patent and that said Letters Patent are hereby corrected as shown below:

| Col. | Line | | |
|---|---|---|---|
| 7 | 20 | 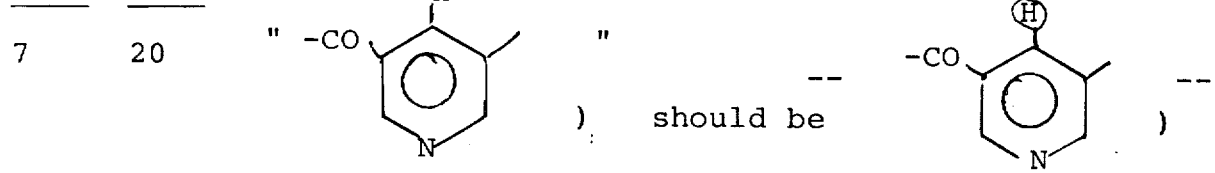 | should be |
| 7 | 30 | 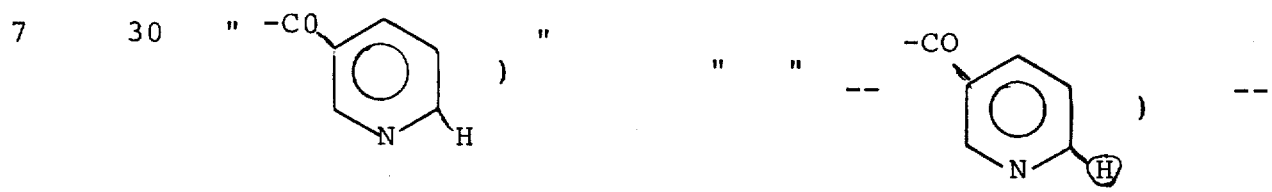 | " " |
| 7 | 40 |  | " " |
| 8 | 7 | Example 5 "-SCH$_2$CH$_2$N-)" should be --SCH$_2$CH$_2$N-)-- |
| 8 | 10 | " " "-CH$_2$NHCO-)" " " -- -CH$_2$NHCO-) -- |
| 8 | 15 | " " 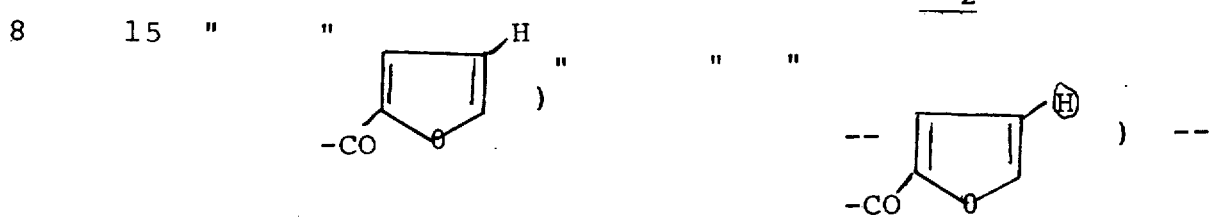 " " |

UNITED STATES PATENT AND TRADEMARK OFFICE
CERTIFICATE OF CORRECTION

PATENT NO. : 4,560,679

DATED : Dec. 24, 1985

INVENTOR(S) : SHIGESHI TOYOSHIMA, RYOICHI UNNO, and KOICHI ITO

It is certified that error appears in the above-identified patent and that said Letters Patent are hereby corrected as shown below:

| Col. | Line | | | |
|---|---|---|---|---|
| 8 | 20 | 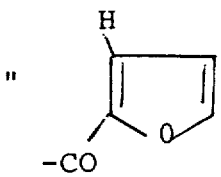 | should be | 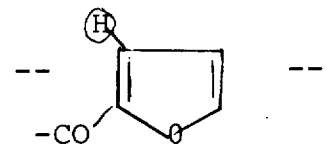 |
| 8 | 30 | 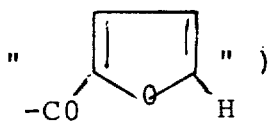 | , | 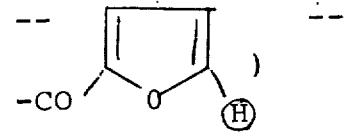 |
| 8 | 65 Example 6 | "-SCH$_2$CH$_2$N-)" | should be | --SCH$_2$CH$_2$N-) -- |
| 8 | " 66 | -CH$_2$NHCO-)" | should be | --CH$_2$NHCO-) -- |
| 10 | Example 8 | "-SCH$_2$CH$_2$N-)" | " " " " " | --SCH$_2$CH$_2$N-) -- |
| 10 | " ' | "-CH$_2$NHCO-) " | " " " " " | -- -CH$_2$NHCO-) -- |
| 10 | Example 9 | "-(CH$_2$)$_6$CH$_3$)" | " " " " " | -- (CH$_2$)$_6$CH$_3$)-- |
| 10 | " " | " -NHCO-CH$_2$-)" | " " " " " | -- -NHCO-CH$_2$-)-- |
| 10 | " " | " -SCH$_2$CH$_2$N-)" | " " " " " | -- -SCH$_2$CH$_2$N-)-- |
| 10 | " " | "-CH$_2$NHCO-)" | " " " " " | -- CH$_2$NHCO-) -- |

UNITED STATES PATENT AND TRADEMARK OFFICE
CERTIFICATE OF CORRECTION

PATENT NO. : 4,560,679

DATED : Dec. 24, 1985

INVENTOR(S) : SHIGESHI TOYOSHIMA, RYOICHI UNNO and KOICHI ITO

It is certified that error appears in the above-identified patent and that said Letters Patent are hereby corrected as shown below:

| Col. | Line | | | | |
|---|---|---|---|---|---|
| 11 | Example 11 | "-SCH$_2$CH$_2$N-)" | should be | -- | -$\underline{SCH}_2$CH$_2$N-)-- |
| 11 | " | " | "NHSO$_2$CH$_3$-)" | " | " | -- NHSO$_2$$\underline{CH}_3$-)-- |
| 11 | " | " | "-SCH$_2$CH$_2$N-)" | " | " | -- -SCH$_2$$\underline{CH}_2$N-)-- |
| 12 | " | 12 | "-SCH$_2$CH$_2$NH-)" | " | " | -- -$\underline{SCH}_2$CH$_2$NH-)-- |
| 12 | " | " | "-CH$_2$NHCO-)" | " | " | -- -$\underline{CH}_2$NHCO-)-- |
| 12 | " | 13 | "-NHCH$_3$)" | " | " | -- -NH$\underline{CH}_3$)-- |
| 13 | " | 14 | "-NHCH$_3$)" | " | " | -- -NH$\underline{CH}_3$)-- |
| 13 | " | " | "SCH$_2$CH$_2$NH-)" | " | " | -- $\underline{SCH}_2$CH$_2$NH-)-- |
| 13 | " | " | "SCH$_2$CH$_2$NH-)" | " | " | --$\underline{SCH}_2$CH$_2$NH-)-- |
| 13 | " | 15 | "$\nu_{max}^{CDC13}$" | " | " | --$\nu_{max}^{CDCl_3}$ -- |
| 14 | " | " | "-SCH$_2$CH$_2$N-)" | " | " | -- -$\underline{SCH}_2$CH$_2$N-)-- |
| 14 | " | " | "-CH$_2$NHCO-)" | " | " | -- -$\underline{CH}_2$NHCO-)-- |
| 14 | " | 16 | "$\nu_{max}^{CDC13}$" | " | " | -- $\nu_{max}^{CHCl_3}$ -- |
| 14 | " | " | "-SCH$_2$CH$_2$N-)" | " | " | -- -SCH$_2$$\underline{CH}_2$N-)-- |
| 14 | " | " | "-NCH$_2$CH=CH)" | " | " | -- -N$\underline{CH}_2$CH=CH)-- |
| 14 | " | " | "-CH$_2$CH=CH$_2$)" | " | " | -- -CH$_2$CH=$\underline{CH}_2$) |
| 15 | " | 17 | "NH-CH$_2$CH=CH$_2$)" | " | " | -- NH-$\underline{CH}_2$CH=CH$_2$)-- |
| 15 | " | " | 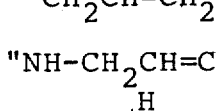 | " | " | 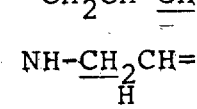 |
| 15 | " | " | 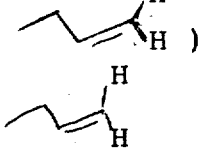 | " | " | 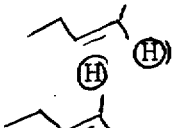 |

UNITED STATES PATENT AND TRADEMARK OFFICE
CERTIFICATE OF CORRECTION

PATENT NO. : 4,560,679

DATED : Dec. 24, 1985

INVENTOR(S) : SHIGESHI TOYOSHIMA, RYOICHI UNNO and KOICHI ITO

It is certified that error appears in the above-identified patent and that said Letters Patent is hereby corrected as shown below:

| Col. | Line | | should be | |
|---|---|---|---|---|
| 15 | Example 18 | "$-SCH_2CH_2N-)$" | " | -- $-SCH_2CH_2N-)$ -- |
| 15 | " " | "$-SCH_2CH_2N-)$" | " " | -- $-SCH_2CH_2N-)$ -- |
| 15 | " " | "$NHCH_2CH=CH_2$)" | " " | -- $NHCH_2CH=CH_2)$ -- |
| 16 | " " | [structure] | " " | [structure] |
| 16 | " " | [structure] | " " | [structure] |
| 16 | " 19 | "$-SCH_2CH_2NH_2)$" | " " | -- $SCH_2CH_2NH_2)$ -- |
| 16 | " " | "$-SCH_2CH_2NH_2)$" | " " | -- $-SCH_2CH_2NH_2)$ -- |
| 18 | " 20 | "$-SCH_2CH_2N-)$" | " " | -- $-SCH_2CH_2N-)$ -- |
| 20 | 61 Cols 2 & 3 | "1190 > 200" | " " | 1190   >200 |
| 22 | Claim 1 | [structure] | " " | [structure] |

UNITED STATES PATENT AND TRADEMARK OFFICE
CERTIFICATE OF CORRECTION

PATENT NO. : 4,560,679  Page 6 of 6
DATED : Dec. 24, 1985
INVENTOR(S) : SHIGESHI TOYOSHIMA, RYOICHI UNNO and KOICHI ITO It is certified that error appears in the above-identified patent and that said Letters Patent is hereby corrected as shown below:

22  Claim 8   " -A-$R_3$ "   "   "   --$\overset{\frown}{A\ \ R_3}$--

[SEAL]

Signed and Sealed this

Sixth Day of May 1986

Attest:

DONALD J. QUIGG

Attesting Officer       Commissioner of Patents and Trademarks